United States Patent [19]

Nagao et al.

[11] Patent Number: 5,710,152

[45] Date of Patent: Jan. 20, 1998

[54] BENZOAZINE DERIVATIVE OR SALT THEREOF AND PHARMACEUTICAL COMPOSTION COMPRISING THE SAME

[75] Inventors: Yoshihiro Nagao; Yoshikuni Ito, both of Narita; Jiro Kotake, Ichikawa; Tadayuki Kouda, Narita; Haruyoshi Honda, Tomisato-machi; Susumu Sato, Narita; Hideaki Matsuda, Abiko, all of Japan

[73] Assignee: SS Pharmaceutical Co., Ltd., Tokyo, Japan

[21] Appl. No.: 791,269

[22] Filed: Jan. 30, 1997

[30] Foreign Application Priority Data

Jan. 31, 1996 [JP] Japan ................... 8-014898

[51] Int. Cl.$^6$ ............ C07D 417/12; A61K 31/54; A61K 31/535; A61K 31/505
[52] U.S. Cl. ............................................. 514/225.2
[58] Field of Search ................ 544/50, 92, 287; 514/225.2, 230.5, 254

[56] References Cited

U.S. PATENT DOCUMENTS 5,478,850  12/1995  Hindley ........................... 514/369

FOREIGN PATENT DOCUMENTS

| 0 590 793 | 4/1994 | European Pat. Off. . |
| 92/07850 | 5/1992 | WIPO ................... 514/369 |
| WO 92/07838 | 5/1992 | WIPO . |
| WO 92/07839 | 5/1992 | WIPO . |

Primary Examiner—Robert Gerstl
Attorney, Agent, or Firm—Oblon, Spivak, McClelland, Maier & Neustadt, P.C.

[57] ABSTRACT

A benzoazine derivative represented by the following formula (1),

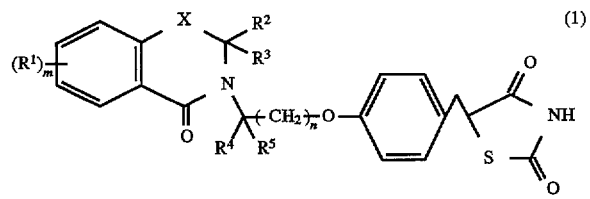

wherein $R^1$ represents an alkyl group, alkoxy group, halogen atom, halogenoalkyl group, amino group, hydroxy group, benzyloxy group which may have a substituent, cyano group, carbamoyl group, acyl group, nitro group, carboxy group, or sulfonamide group; $R^2$ and $R^3$ may be the same or different and each individually represents a hydrogen atom or an alkyl group, or $R^2$ and $R^3$ indicate in combination an alkylene group having 2–7 carbon atoms; $R^4$ and $R^5$ may be the same or different and each individually represents a hydrogen atom or an alkyl group; X denotes O, S, or N—$R^6$ (wherein $R^6$ represents a hydrogen atom, an alkyl group, or an aryl group or pyridyl group which may have a substituent); m is an integer from 0 to 4; and n is an integer from 1 to 3, or a salt of the benzoazine derivative. The compound exhibits superior effects for reducing blood glucose value, plasma insulin value, and plasma triglyceride value, and is useful as a medicament for preventing or treating diabetes, hyperlipidemia, and obesity.

4 Claims, No Drawings

BENZOAZINE DERIVATIVE OR SALT THEREOF AND PHARMACEUTICAL COMPOSTION COMPRISING THE SAME

BACKGROUND OF THE INVENTION

1. Field of the Invention

The present invention relates to a novel benzoazine derivative or a salt thereof and a pharmaceutical composition comprising the benzoazine derivative or the salt.

2. Description of the Background Art

Non-insulin-dependent diabetes mellitus (NIDDM) is a disease induced by insulin resistance in the target tissue of the insulin or impaired insulin secretion from the pancreatic β cell. Sulfonylurea compounds and insulin which have conventionally been used for the treatment of NIDDM mainly improve impaired insulin secretion. Although the sulfonylurea compounds exhibit a strong antidiabetic action based on pancreatic and ex-pancreatic activities, prudent care should be taken when administering them because these compounds may sometimes induce serious hypoglycemia.

In recent years, the significance of insulin resistance in NIDDM has been realized and this has created a desire for the development of a medication which exhibits an antidiabetic action without stimulating insulin secretion by reducing insulin resistance in the target tissues of the insulin. Thiazolidine derivatives such as troglitazone and pioglitazone have been developed as compounds which possess such an action (Japanese Patent Applications Laid-open No. 22636/1980, No. 51189/1985, and No. 157522/1994).

Some other thiazolidine derivatives with a bicyclic lactam structure or a cyclic urethane structure which exhibit similar actions have been reported (WO 92/07838, WO 92/07839, and WO 92/07850).

However, the effect of these compounds with insulin resistance-reducing activity on decreasing blood glucose or lipids is not sufficient. Development of a compound which exhibits a stronger antidiabetic action has been desired.

An object of the present invention is therefore to provide a novel compound which exhibits superior antidiabetic action as compared with conventionally known compounds and is useful as a medication for preventing and treating diabetes, hyperlipidemia, obesity, and the like.

In view of this background, the inventors of the present invention have synthesized various compounds and studied their pharmaceutical actions. As a result, the inventors have found that novel benzoazine derivatives shown by the following general formula (1) exhibit superior blood glucose and lipid reduction actions and are useful as a medication for preventing and treating diabetes, hyperlipidemia, obesity, and the like. This finding has led to the completion Of the present invention.

SUMMARY OF THE INVENTION

Accordingly, an object of the present invention is to provide a benzoazine derivative represented by the following formula (1),

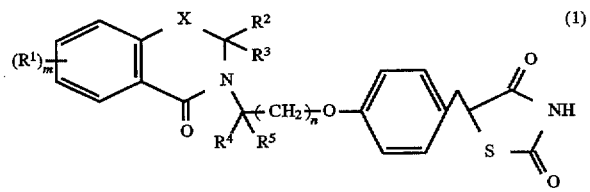

wherein $R^1$ represents an alkyl group, alkoxy group, halogen atom, halogenoalkyl group, amino group, hydroxy group, benzyloxy group which may have a substituent, cyano group, carbamoyl group, acyl group, nitro group, carboxy group, or sulfonamide group; $R^2$ and $R^3$ may be the same or different and each individually represents a hydrogen atom or an alkyl group, or $R^2$ and $R^3$ indicate in combination an alkylene group having 2-7 carbon atoms; $R^4$ and $R^5$ may be the same or different and each individually represents a hydrogen atom or an alkyl group; X denotes O, S, or N—$R^6$ (wherein $R^6$ represents a hydrogen atom, an alkyl group, or an aryl group or pyridyl group which may have a substituent); m is an integer from 0 to 4; and n is an integer from 1 to 3, or a salt of the benzoazine derivative.

Another object of the present invention is to provide a pharmaceutical composition comprising this benzoazine derivative or the salt thereof as an active component.

Still another object of the present invention is to provide a method for reducing blood glucose or lipids in a subject which comprises administering the benzoazine derivative or the salt thereof to the subject.

Other object, features and advantages of the invention will hereinafter become more readily apparent from the following description.

DETAILED DESCRIPTION OF THE INVENTION AND PREFERRED EMBODIMENTS

Given as examples of the alkyl group represented by $R^1$ in the above-mentioned general formula (1) are linear or branched alkyl groups having 1–6 carbon atoms such as methyl, ethyl, n-propyl, isopropyl, n-butyl, isobutyl, sec-butyl, t-butyl, n-pentyl, isopentyl, and n-hexyl groups. Of these, methyl, ethyl, and t-butyl groups are particularly preferred. Given as examples of the alkoxy group are linear or branched alkoxy groups having 1-6 carbon atoms such as methoxy, ethoxy, n-propoxy, isopropoxy, n-butoxy, isobutoxy, sec-butoxy, t-butoxy, n-pentyloxy, isopentyloxy, and n-hexyloxy groups. Methoxy and ethoxy groups are particularly preferred among these. A fluorine atom, chlorine atom, iodine atom, and bromine atom are given as examples of the halogen atom. Fluoroalkyl chloroalkyl, bromoalkyl, and iodoalkyl groups are given as examples of the halogenoalkyl group, but not limited to these. A trifluoromethyl group is a particularly preferred halogenoalkyl group.

The substituent for the benzyloxy group which may have a substituent is not specifically limited. An alkyl group, alkoxy group, alkoxycarbonyl group, alkylamino group, carboxy group, and the like are given as examples. The specific alkyl groups and alkoxy groups mentioned above can be given as examples of the alkyl group, the alkoxy group, the alkoxy group of the alkoxycarbonyl group, the alkyl group of the alkylamino group, which are the substituent for the benzyloxy group. As examples of the acyl group, formyl, acetyl, propionyl, butyryl, and benzoyl groups are given.

Particularly preferred groups for $R^1$ in the general formula (1) are a hydrogen atom, alkyl groups, and alkoxy groups.

As the specific alkyl groups for $R^2$ and $R^3$ in the above general formula (1), on the other hand, the alkyl groups mentioned for $R^1$ are given. Although there are no specific limitations to the alkylene groups with 2–7 carbon atoms which are formed by $R^2$ and $R^3$ together, a dimethylene group, trimethylene group, tetramethylene group, pentamethylene group, hexamethylene group, and the like are given as examples.

Preferred groups for $R^2$ or $R^3$ in the general formula (1) are a hydrogen atom and alkyl groups.

The same alkyl groups given above as the examples for $R^1$ are given as the alkyl groups for $R^4$ and $R^5$ in the general formula (1).

There are also no specific limitation to the alkyl group for R in the group N—$R^6$. Those exemplified for $R^1$ are applicable. As examples of the aryl group which may have a substituent, a phenyl group and naphthyl group are given, with the phenyl group being more preferred. Given as examples of the substituent for this aryl group are a halogen atom, alkyl group, phenyl group, alkoxy group, halogenoalkyl group, hydroxyalkyl group, hydroxy group, amino group, nitro group, cyano group, alkoxycarbonyl group, alkoxycarbonylalkylamino group, carboxy group, and the like. Also, there are no specific limitation to the pyridyl group which may have a substituent. Pyridyl groups having the same substituent groups as those mentioned above as the substituent for the aryl group are applicable.

Any of 0, 1, or 2 is desirable as the number of the substituent (m) in the above-mentioned general formula (1). The substitution position may be 5, 6, 7, or 8.

1 or 2 is desirable as n in the above-mentioned general formula (1), with 1 being more preferred.

There are no specific limitations to the salt for the benzoazine derivative (1) in the present invention, so long as the salt is pharmaceutically acceptable. Given as preferred examples of the salt are alkali metal salts such as potassium salt and sodium salt, alkaline earth metal salt such as calcium salt, and the like. Also, given as examples of the salt where X is N—$R^6$ in the compound (1) of the present invention are a hydrogen halide such as hydrofluoride, hydrochloride, hydrobromide, and hydroiodide; inorganic salts such as carbonate, nitrate, perchlorate, sulfate, and phosphate; a lower alkyl sulfonate such as methane sulfonate, trifluoromethane sulfonate, and ethane sulfonate; an aryl sulfonate such as benzene sulfonate and p-toluene sulfonate; an organic acid salt such as fumarate, succinate, citrate, tartrate, oxalate, and maleate; and an amino acid salt such as glutamate and aspartate.

The present invention also includes hydrates, solvates of various pharmaceutically acceptable solvents, and various forms of crystals of the compound represented by the above general formula (1), as well as the stereoisomers based on the asymmetrical carbon atom in the general formula (1).

The benzoazine derivatives (1) of the present invention can be prepared by any one of the following processes.

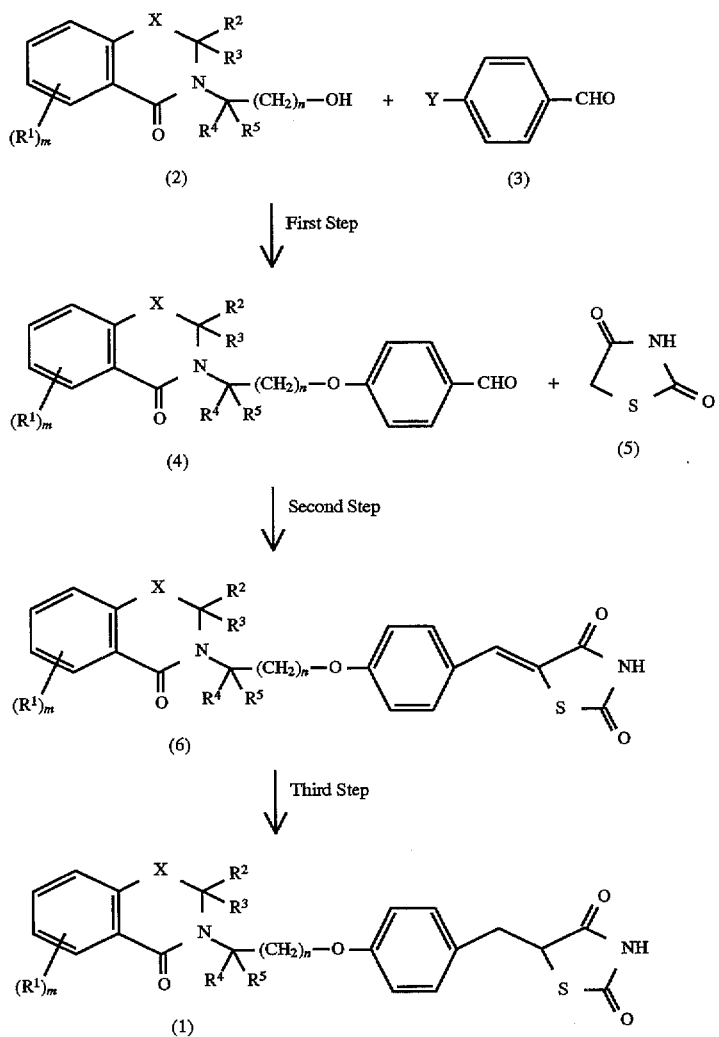

In the above formulas, $R^1$, $R^2$, $R^3$, $R^4$, $R^5$, X, m, and n have the same meanings as previously defined, and Y indicates a halogen atom.

According to the above reaction scheme, a compound of the formula (2) is reacted with p-halogenobenzaldehyde of the formula (3) to produce a compound of the formula (4) (first step), then this compound (4) is subjected to a condensation with 2,4-thiazolidinedione (compound (5)) to produce a condensate which is represented by the formula (6) (second step). The compound (6) is then reduced to produce the compound (1) of the present invention (third step). Each step of the process 1 will now be described.

(First step)

The compound (2) which is the starting material can be manufactured by a method described, for example, in Journal of Medicinal Chemistry vol. 11, page 1038 (1968), and Journal of Medicinal Chemistry vol.38, page 130 (1995), etc. This compound (2) is reacted with p-halogenobenzaldehyde (3) in the presence of a suitable base and a solvent to obtain the compound (4). Given as specific examples of the halogen atom Y in the p-halogenObenzaldehyde (3) are a fluorine atom, chlorine atom, bromine atom, and iodine atom, with the fluorine atom being especially desirable. Specific examples of the p-halogenobenzaldehyde (3) include p-fluorobenzaldehyde, p-chlorobenzaldehyde, p-bromobenzaldehyde, p-iodobenzaldehyde, and the like.

Sodium hydride, potassium t-butoxide, sodium hydroxide, potassium hydroxide, and the like are given as examples of the base used in the reaction of the compound (2) and compound (3). The solvent used in the reaction may be any solvent which does not affect the reaction, and include ethers such as tetrahydrofuran and dioxane; hydrocarbons such as benzene and toluene; amides such as dimethylformamide, dimethylacetamide, and N-methyl-α-pyrrolidone; and sulfoxides such as dimethyl sulfoxide. The reaction may be carried out either under ice cooling or under heating while refluxing the reactants for about 0.5 to 24 hours. Most suitably, this step is carried out by adding sodium hydride to a dimethylsulfoxide solution of the compound (2), stirring the mixture for about 1 hour at a temperature of about 40° C., adding the compound (3) to the resulting mixture, and stirring for about 1-2 hours at about room temperature.

(Second step)

The compound (4) is reacted with 2,4-thiazolidinedione (5) in the presence Of a suitable solvent and a catalyst under the conditions of the Knoevenagel condensation to obtain the compound (6).

There are no limitations to the solvent which is used in the reaction inasmuch as the solvent does not affect the reaction. Specific examples of such a solvent include hydrocarbons such as benzene, toluene, and xylene; amides such as dimethylformamide, dimethylacetamide, N-methyl-α-pyrolidone; and alcohols such as ethanol, propanol, and ethoxy ethanol. As the catalyst used in the reaction, piperidine and acetic acid, piperidinium acetate, piperidinium benzoate, or the like are given. The reaction is carried out at room temperature or with heating while refluxing for about 0.5 to 24 hours. Most suitably, this second step is carried out by reacting the compound (4) and 2,4-thiazolidinedione (5) in toluene in the presence of a catalytic amount of piperidine and acetic acid in a Dean-Stark apparatus while refluxing with heating for about 2-4 hours.

(Third step)

The compound (1) can be produced by hydrogenating the compound (6) in a suitable solvent in the presence of a hydrogenation catalyst. A palladium catalyst, such as palladium-carbon, palladium-black, or palladium hydroxide, or a platinum catalyst, such as platinum oxide or platinum black, can be used as the catalyst. There are no limitations to the solvent which is used in the reaction inasmuch as the solvent does not affect the reaction. Specific examples include ethanol, dioxane, dimethylformamide, acetic acid, and the like. The reaction is carried out under heating at a temperature from room temperature to about 80°–100° C. under atmospheric pressure or under pressure.

Process 2

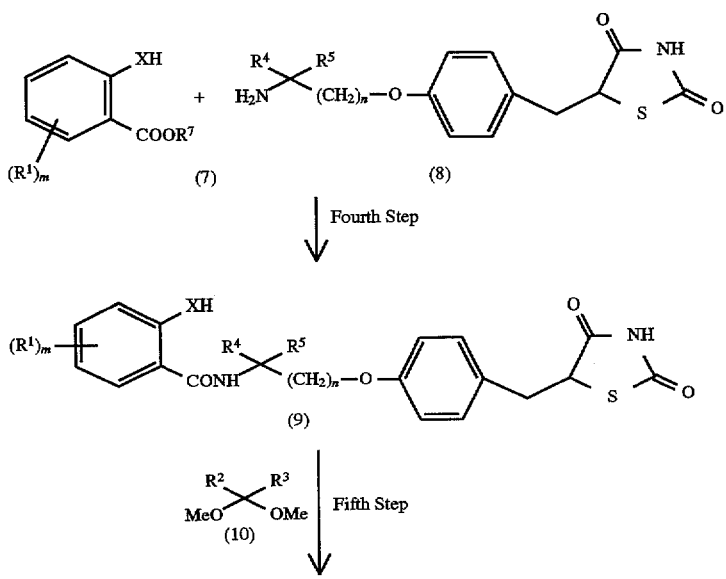

-continued
Process 2

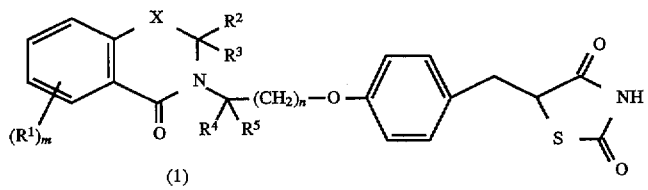

In the above reaction formulas, $R^1$, $R^2$, $R^3$, $R^4$, $R^5$, X, m, and n are the same as previously defined, and $R^7$ represents an alkyl group.

According to the above reaction formulas, a benzoic acid derivative which is shown by the formula (7) is reacted with a compound of the formula (8) to produce a compound represented by the formula (9) (Fourth step). The compound (9) is then reacted with an acetal compound of the formula (10) to cyclizate, thereby obtaining the compound (1) of the present invention (fifth step). Each step of the Process 2 will now be described.

(Fourth step)

The benzoic acid derivative (7) is reacted with the compound (8) in the presence or absence of a solvent to produce the compound (9). The above-described alkyl groups are given as the alkyl group ($R^7$) in the ester group of the benzoic acid derivative (7). Various derivatives, such as methyl salicylate, ethyl 5-chlorosalicylate, methyl 4-methylsalicylate, methyl N-methylanthranilate, and methyl thiosalicylate, are given as examples of a preferred benzoic acid derivative (7).

The compound (8) can be prepared by a known method such as a method disclosed by Japanese Patent Application Laid-open No. 13076/1989, Japanese Patent Application Laid-open No. 157522/1994, or the like.

Any solvent may be used in the reaction of the benzoic acid derivative (7) and the compound (8) without any specific limitations so long as such a solvent does not adversely affect the reaction. Included in the examples of such a solvent are ethers such as tetrahydrofuran and dioxane, hydrocarbons such as benzene and toluene, amides such as dimethylformamide, dimethylacetamide, and N-methyl-α-pyrrolidone, and sulfoxides such as dimethyl sulfoxide. The reaction is carried out at room temperature or with heating while refluxing for about 0.5 to 24 hours.

(Fifth step)

The compound (9) is reacted with the acetal compound (10) in the presence or absence of a solvent using an acid catalyst to produce the compound (1) of the present invention. The acetal Compound (10) can be prepared by treating a corresponding aldehyde compound or ketone compound by a known method, such as the method disclosed by T. W. Green (Protective Groups in Organic Synthesis) and the like. Specific examples of this acetal compound (10) include acetone dimethylacetal, acetaldehyde dimethylacetal, and cyclic acetals such as cyclopentanone dimethylacetal.

Any solvent may be used in the reaction of the compound (9) and the acetal compound (10) without any specific limitations so long as such a solvent does not adversely affect the reaction. Included in the examples of such a solvent are ethers such as tetrahydrofuran and dioxane, hydrocarbons such as benzene and toluene, amides such as dimethylformamide, dimethylacetamide, and N-methyl-α-pyrrolidone, and sulfoxides such as dimethyl sulfoxide. The reaction is carried out at room temperature or with heating while refluxing for about 0.5 to 24 hours.

Process 3

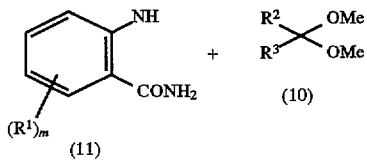

Sixth Step

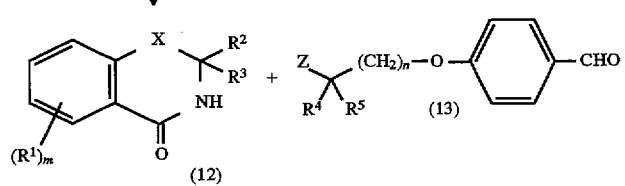

Seventh Step

-continued
Process 3

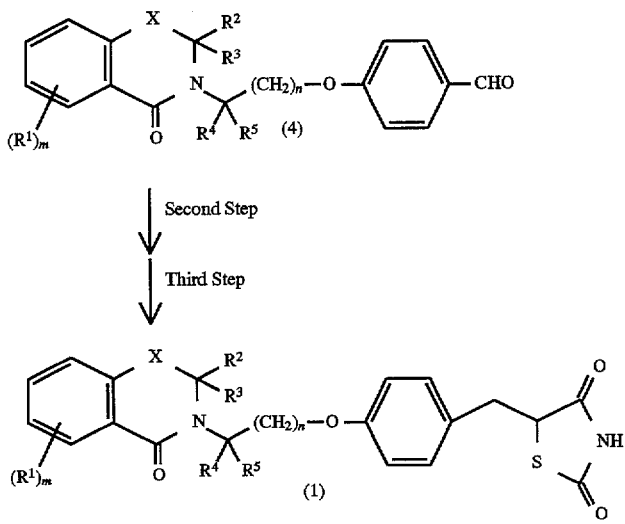

In the above reaction formulas, $R^1$, $R^2$, $R^3$, $R^4$, $R^5$, X, m, and n have the same meanings as previously defined, and Z is a leaving group.

According to the above reaction formulas, the carboxamide derivative of the formula (11) and the acetal compound (10) are cyclized to obtain the compound of the formula (12) (sixth step). The 3-position of this compound (12) is alkylated using an aldehyde compound of the formula (13) to produce the compound of the general formula (4) (seventh step). The compound (1) of the present invention is then produced according to the Process 1. Each step of the Process 3 will now be described.

(Sixth step)

The carboxamide derivative (11) is reacted with the compound (10) in the presence or absence of a solvent using an acid catalyst to produce the compound (12).

Salicylamide, 5-chlorosalicylamide, thiosalicylamide, 2-anilinobenzamide, 2-aminobenzamide, and the like can be used as the carboxamide derivative (11). As the acetal compound (10), the compounds described in the Process 2 can be used.

Any solvent can be used in the reaction of the carboxamide derivative (11) and the acetal compound (10) without any specific limitations so long as such a solvent does not adversely affect the reaction. Included in the examples of such a solvent are hydrocarbons such as benzene, toluene, and xylene, and ethers such as tetrahydrofuran and dioxane. p-Toluene-sulfonic acid, methanesulfonic acid, or the like are given as examples of the acid catalyst. The reaction is carried out while heating or refluxing for about 0.5 to 24 hours. Most preferably, this sixth step is carried out by reacting the carboxamide derivative (11) and an excess amount of the acetal compound (10) in the presence of p-toluenesulfonic acid for about 2 to 4 hours while refluxing.

(Seventh Step)

The compound (12) is reacted with the compound (13) in the presence of a suitable base and a solvent to obtain the compound (4).

The compound (13) is prepared by the halogenation or sulfonylation of the hydroxyl group in the benzaldehyde with a hydroxyalkoxy group at the para-position, such as, for example, 4-(2-hydroxyethoxy)benzaldehyde. As the leaving group (Z), halogen atoms such as a chlorine atom, bromine atom, or iodine atom; sulfonyloxy groups such as a methanesulfonyloxy group, p-toluenesulfonyloxy group, trifluoromethanesulfonyloxy group; and the like are given, with the methanesulfonyloxy group being especially desirable. Sodium hydride, potassium t-butoxide, sodium hydroxide, potassium hydroxide, potassium carbonate, and the like can be given as examples of the base used in the reaction of the compound (12) and the compound (13). The solvent used in the reaction may be any solvent which does not affect the reaction, and includes ethers such as tetrahydrofuran and dioxane; hydrocarbons such as benzene and toluene; amides such as dimethylformamide, dimethylacetamide, and N-methyl-α-pyrrolidone; and sulfoxides such as dimethyl sulfoxide. The reaction may be carried out either under ice cooling or under heating while refluxing the reactants, most preferably, by stirring a mixture of the compound (12) and compound (13) while heating for about 2–5 hours at a temperature of about 80°–90° C. in dimethylformamide in the presence of potassium carbonate.

The compound (4) thus obtained can be converted into the compound (1) of the present invention according to the second step and third step of the Process 1.

The compound (1) of the present invention prepared in any one of the above-described processes can be easily purified and collected as a liquid product or crystals by means of conventional purification methods such as recrystallization, distillation, chromatography, and the like.

The resulting compound (1) of the present invention exhibits superior antidiabetic action and lipid reducing action, and is useful as a drug for treating or preventing diabetes, hyperlipidemia, and obesity.

The pharmaceutical composition comprising the compound (1) of the present invention can be prepared by formulating an effective amount of this compound or the salt with suitable additives known in the art as pharmaceutically acceptable additives, such as excipients, binding agents, disintegrators, lubricants, solubilizers, and suspension agents depending on the intended pharmacological action, purpose of administration, dosing form, and the like. The dosing form may be, for example, tablets, capsules, granules, a powder, or a syrup for oral administration, or injection, an ophthalmic preparation, or suppository for parenteral administration. Although the dose of the pharmaceutical composition of the present invention varies depending on the symptom, age, weight, and the like of the patient, and the dosing method, such a dose may usually be selected from the range of 1 mg to 1000 mg of the compound (1) per day for an adult.

The application of the compound (1) of the present invention is not limited to humans, but the compound can be used as a medicament for other mammals.

The compound (1) of the present invention possesses the action of reducing insulin resistance in target tissues of the insulin. This action is extremely strong as compared with other known compounds. The compound (1) of the present invention therefore exhibits an antidiabetic effect and a lipid reducing effect based on this action, and is useful as a drug for treating and preventing diabetes, hyperlipidemia, and obesity.

Other features of the invention will become apparent in the course of the following description of the exemplary embodiments which are given for illustration of the invention and are not intended to be limiting thereof.

EXAMPLES

Preparation Example 1

Preparation of 4-[2-(4-oxo-3,4-dihydro-2H-1,3-benzoxazin-3-yl)-ethoxy]benzaldehyde (compound (4A))

0.58 g (3.0 mM) of 2-(4-oxo-3,4-dihydro-2H-1,3-benzoxazin-3-yl)-ethanol was dissolved in 5.0 ml of dimethyl sulfoxide. After the addition of 0.18 g (4.5 mM) of sodium hydride (oil) under ice cooling, the mixture was stirred for one hour while heating at 40° C. Then, 0.56 g (4.5 mM) of p-fluorobenzaldehyde in 5.0 ml of benzene was gradually added dropwise under ice cooling. After the addition, the mixture was allowed to stand room temperature while stirring for one hour. After the reaction, the reaction mixture was poured into ice water and extracted twice with ethyl acetate. The oil phase was combined and washed once with water, dried over magnesium sulfate, and concentrated under vacuum. The residue was purified with a silica gel column (eluent, hexane:ethyl acetate=5:1) to obtain 0.56 g (yield 62%) of colorless crystals of the title compound.

Preparation Example 2

Reactions were carried out in the same manner as in the Preparation Example 1, except that instead of 2-(4-oxo-3,4-dihydro-2H-1,3-benzoxazin-3-yl)ethanol, the following compounds were used as the raw material compounds: 3-(4-oxo-3,4-dihydro-2H-1,3-benzoxazin-3-yl)propanol, 2-(2,2-dimethyl-4-oxo-3,4-dihydro-2H-1,3-benzoxazin-3-yl)ethanol, 2-(2-methyl-4-oxo-3,4-dihydro-2H-1,3-benzoxazin-3-yl)ethanol, 2-(7-methyl-4-oxo-3,4-dihydro-2H-1,3-benzoxazin-3-yl)ethanol, 2-(6-methoxy-4-oxo-3,4-dihydro-2H-1,3-benzoxazin-3-yl)ethanol, 2-(8 methoxy-4-oxo-3,4-dihydro-2H-1,3-benzoxazin-3-yl)ethanol, 2-(6-chloro-4-oxo-3,4-dihydro-2H-1,3-benzoxazin-3-yl)ethanol, 2-(7-methoxy-4-oxo-3,4-dihydro-2H-1,3-benzoxazin-3-yl) ethanol, and 2-(6-nitro-4-oxo-3,4-dihydro-2H-1,3-benzoxazin-3-yl)ethanol, respectively to produce the following compounds:

4-[3-(4-oxo-3,4-dihydro-2H-1,3-benzoxazin-3-yl)propoxy] benzaldehyde (Compound 4B), 4-[2-(2,2-dimethyl-4-oxo-3,4-dihydro-2H-1,3-benzoxazin-3-yl)ethoxy]benzaldehyde (Compound 4C), 4-[2-(2-methyl-4-oxo-3,4-dihydro-2H-1,3-benzoxazin-3-yl) ethoxy]benzaldehyde (Compound 4D), 4-[2-(7-methyl-4-oxo-3,4-dihydro-2H-1,3-benzoxazin-3-yl) ethoxy]benzaldehyde (Compound 4E), 4-[2-(6-methoxy-4-oxo-3,4-dihydro-2H-1,3-benzoxazin-3-yl)ethoxy]benzaldehyde (Compound 4F), 4-[2-(8-methoxy-4-oxo-3,4-dihydro-2H-1,3-benzoxazin-3-yl)ethoxy]benzaldehyde (Compound 4G), 4-[2-(6-chloro-4-oxo-3,4-dihydro-2H-1,3-benzoxazin-3-yl) ethoxy]benzaldehyde (Compound 4H), 4-[2-(7-methoxy-4-oxo-3,4-dihydro-2H-1,3-benzoxazin-3-yl)ethoxy]benzaldehyde (Compound 4I), and 4-[2-(6-nitro-4-oxo-3,4-dihydro-2H-1,3-benzoxazin-3-yl) ethoxy]benzaldehyde (Compound 4J).

Preparation Example 3

Preparation of 4-[2-(4-oxo-1-phenyl-1,2,3,4-tetrahydroquinazolin-3-yl)ethoxy]benzaldehyde (Compound 4K)

1.2 g of 2-(4-oxo-1-phenyl-1,2,3,4-tetrahydroquinazolin-3-yl)ethanol was dissolved in 8 ml of dimethyl sulfoxide. 0.27 g of 60% sodium hydride (oil) was added under ice cooling and the mixture was stirred for one hour at 40° C. Then, 0.84 g of p-fluorobenzaldehyde in 8 ml of benzene was gradually added dropwise and the mixture was allowed to stand room temperature while stirring for one hour. The reaction mixture was processed in the same manner as in the Preparation Example 1 to obtain 0.84 g (yield 50.4%) of the title compound as colorless crystals.

Preparation Example 4

Reactions were carried out in the same manner as in the Preparation Example 3, except that 2-(4-oxo-1-phenyl-1,2,3,4-tetrahydroquinazolin-3-yl)ethanol was replaced by 2-(4-oxo-1-methyl-1,2,3,4-tetrahydroquinazolin-3-yl) ethanol or 2-[4-oxo-1-(2-pyridyl)-1,2,3,4-tetrahydroquinazolin-3-yl] ethanol, to produce 4-[2-(4-oxo-1-methyl-1,2,3,4)-tetrahydroquinazolin-3-yl)ethoxy]benzaldehyde (Compound 4L) and 4-[2-[4-oxo-1-(2-pyridyl)-1,2,3,4-tetrahydroquinazolin-3-yl]ethoxy]benzaldehyde (Compound 4M), respectively.

NMR data for the Compound 4A to Compound 4M obtained in the Preparation Examples 1–4 are listed in Table 1.

TABLE 1

| Compound No. | $(R^1)m$ | $R^2$ | $R^3$ | $R^4$ | $R^5$ | X | n | $^1$H-NMR(CDCl$_3$, δ) |
|---|---|---|---|---|---|---|---|---|
| 4A | — | H | H | H | H | O | 1 | 3.99(2H, t) 4.36(2H, t) 5.37(2H, s) 6.97–7.01(3H, m) 7.12(1H, br t) 7.45(1H, ddd) 7.84(2H, d) 7.95(1H, dd) 9.89(1H, s) |
| 4B | — | H | H | H | H | O | 2 | 2.18(2H, q) 3.74(2H, t) 4.15(2H, t) 5.20(2H, s) 6.95–7.00(3H, m) 7.11–7.13(1H, m) 7.41–7.45(1H, m) 7.81(2H, d) 7.94(1H, dd) 9.87(1H, s) |
| 4C | — | Me | Me | H | H | O | 1 | 1.64(6H, s) 3.92(2H, t) 4.32(2H, t) 6.88–7.19(4H, m) 7.39–7.58(2H, m) 7.80–8.00(2H, m) 9.92(1H, s) |

TABLE 1-continued

| Compound No. | (R¹)m | R² | R³ | R⁴ | R⁵ | X | n | ¹H-NMR(CDCl₃, δ) |
|---|---|---|---|---|---|---|---|---|
| 4D | — | Me | H | H | H | O | 1 | 1.68(3H, d) 3.72(1H, ddd) 4.17(1H, ddd) 4.26–4.37(2H, m) 5.66(1H, q) 6.93(1H, dd) 7.01(2H, d) 7.09(1H, dt) 7.44(1H, dt) 7.83(2H, d) 7.93(1H, dd) 9.88(1H, s) |
| 4E | 7-Me | H | H | H | H | O | 1 | 2.37(3H, s) 3.97(2H, t) 4.29(2H, t) 5.34(2H, s) 6.92(1H, d) 6.98–7.00(3H, m) 7.81–7.84(3H, m) 9.88(1H, s) |
| 4F | 6-OMe | H | H | H | H | O | 1 | NMR not measured. |
| 4G | 8-OMe | H | H | H | H | O | 1 | 3.91(3H, s) 4.00(2H, t) 4.29(2H, t) 5.42(2H, s) 6.98(2H, d) 7.05–7.09(2H, m) 7.55–7.56(1H, m) 7.83(2H, d) 9.88(1H, s) |
| 4H | 6-Cl | H | H | H | H | O | 1 | 3.99(2H, t) 4.29(2H, t) 5.37(2H, s) 6.94(1H, d) 6.99(2H, d) 7.40(1H, dd) 7.84(2H, d) 7.91(1H, d) 9.89(1H, s) |
| 4I | 7-OMe | H | H | H | H | O | 1 | 3.83(3H, s) 3.96(2H, t) 4.28(2H, t) 5.35(2H, s) 6.45(1H, d) 6.66(1H, dd) 6.99(2H, d) 7.82–7.87(3H, m) 9.88(1H, s) |
| 4J | 6-NO₂ | H | H | H | H | O | 1 | 4.03(2H, t) 4.32(2H, t) 5.50(2H, s) 6.95–7.17(3H, m) 7.85(2H, d) 8.33(1H, dd) 8.85(1H, d) 9.89(1H, s) |
| 4K | — | H | H | H | H | N—phenyl | 1 | 3.92(2H, t) 4.25(2H, t) 5.18(2H, s) 6.53–7.56(10H, m) 7.75(2H, d) 8.02(1H, dd) 9.85(1H, s) |
| 4L | — | H | H | H | H | N—Me | 1 | 2.90(3H, s) 3.95(2H, t) 4.32(2H, t) 4.62(2H, s) 6.56–7.21(4H, m) 7.39(1H, ddd) 7.67–8.17(3H, m) 9.87(1H, s) |
| 4M | — | H | H | H | H | N—pyridyl | 1 | 3.96(2H, t) 4.25(2H, t) 5.61(2H, s) 6.75–7.88(10H, m) 8.08(1H, dd) 8.33(1H, dd) 9.84(1H, s) |

Preparation Example 5

Preparation of 5-[4-[2-(4-oxo-3,4-dihydro-2H-1,3-benzoxazin-3-yl)ethoxy]benzylidene]-2,4-thiazolidinedione (Compound 6A)

5.0 g (17 mM) of 4-[2-(4-oxo-3,4-dihydro-2H-1,3-benzoxazin-3-yl)ethoxy]benzaldehyde (Compound 4A) and 2.1 (18 mM) of 2,4-thiazolidinedione were dissolved in 150 ml of toluene. After the addition of a catalytic amount of acetic acid and piperidine, the mixture was reacted for two hours with heating while refluxing in a Dean Stark apparatus. After confirming completion of the reaction by TLC, the reaction mixture was gradually returned to room temperature. The resulting crystals were collected by filtration and washed with a small amount of toluene and then with hexane, and dried under vacuum at 50° C, to obtain 5.8 g (yield 87%) of the title compound as pale yellow crystals.

Preparation Example 6

Reactions were carried out in the same manner as the Preparation Example 5, except that instead of the 4-[2-(4-oxo-3,4-dihydro-2H-1,3-benzoxazin-3-yl)ethoxy]benzaldehyde (Compound 4A), the following compounds were used as the raw material compounds: 4-[3-(4-oxo-3,4-dihydro-2H-1,3-benzoxazin-3-yl)propoxy]benzaldehyde (Compound 4B), 4-[2-(2,2-dimethyl-4-oxo-3,4-dihydro-2H-1,3-benzoxazin-3-yl)ethoxy]benzaldehyde (Compound 4C), 4-[2-(2-methyl-4-oxo-3,4-dihydro-2H-1,3-benzoxazin-3-yl)ethoxy]benzaldehyde (Compound 4D), 4-[2-(7-methyl-4-oxo-3,4-dihydro-2H-1,3-benzoxazin-3-yl)ethoxy]benzaldehyde (Compound 4E), 4-[2-(6-methoxy-4-oxo-3,4-dihydro-2H-1,3-benzoxazin-3-yl)ethoxy]benzaldehyde (Compound 4F), 4-[2-(8-methoxy-4-oxo-3,4-dihydro-2H-1,3-benzoxazin-3-yl)ethoxy]benzaldehyde (Compound 4G), 4-[2-(6-chloro-4-oxo-3,4-dihydro-2H-1,3-benzoxazin-3-yl)ethoxy]benzaldehyde (Compound 4H), 4-[2-(7-methoxy-4-oxo-3,4-dihydro-2H-1,3-benzoxazin-3-yl)ethoxy]benzaldehyde (Compound 4I), 4-[2-(6-nitro-4-oxo-3,4-dihydro-2H-1,3-benzoxazin-1,3-yl)ethoxy]benzaldehyde (Compound 4J), 4-[2-(4-oxo-1-phenyl-1,2,3,4-tetrahydroquinazolin-3-yl)ethoxy]benzaldehyde (Compound 4K), 4-[2-(4-oxo-1-methyl-1,2,3,4-tetrahydroquinazolin-3-yl)ethoxy]benzaldehyde (Compound 4L), and 4-[2-[4-oxo-1-(2-pyridyl)-1,2,3,4-tetrahydroquinazolin-3-yl]ethoxy]benzaldehyde (Compound 4M), respectively to produce the following compounds:

5-[4-[3-(4-oxo-3,4-dihydro-2H-1,3-benzoxazin-3-yl)propoxy]benzylidene]-2,4-thiazolidinedione (Compound 6B), 5-[4-[2-(2,2-dimethyl-4-oxo-3,4-dihydro-2H-1,3-benzoxazin-3-yl)ethoxy]benzylidene]-2,4-thiazolidinedione (Compound 6C), 5-[4-[2-(2-methyl-4-oxo-3,4-dihydro-2H-1,3-benzoxazin-3-yl)ethoxy]benzylidene]-2,4-thiazolidinedione (Compound 6D), 5-[4-[2-(7-methyl-4-oxo-3,4-dihydro-2H-1,3 -benzoxazin-3-yl)ethoxy]benzylidene]-2,4-thiazolidinedione (Compound 6E), 5-[4-[2-(6-methoxy-4-oxo-3,4-dihydro-2H-1,3-benzoxazin-3-yl)ethoxy]benzylidene]-2,4-thiazolidinedione (Compound 6F), 5-[4-[2-(8-methoxy-4-oxo-3,4-dihydro-2H-1,3-benzoxazin-3-yl)ethoxy]benzylidene]-2,4-thiazolidinedione (Compound 6G), 5-[4-[2-(6-chloro-4-oxo-3,4-dihydro-2H-1,3-benzoxazin-3-yl)ethoxy]benzylidene]-2,4-thiazolidinedione ( Compound 6H), 5-[4-[2-(7-methoxy-4-oxo-3,4-dihydro-2H, 3-benzoxazin-3-yl)ethoxy]benzylidene]-2,4-thiazolidinedione (Compound 6I), 5-[4-[2-(6-nitro-4-oxo-3,4-dihydro-2H-1,3-benzoxazin-3-yl)ethoxy]benzylidene]-2,4-thiazolidinedione (Compound 6J), 5-[4-[2-(4-oxo-1-phenyl-1,2,3,4-tetrahydroquinazolin-3-yl) ethoxy]benzylidene]-2,4-thiazolidinedione (Compound 6K), 5-[4-[2-(4-oxo-1-methyl-1,2,3,4-tetrahydroquinazolin-3-yl)ethoxy]benzylidene]-2,4-thiazolidinedione (Compound 6L), and
5-[4-[2-[4-oxo-1-(2-pyridyl)-1,2,3,4-tetrahydroquinazolin-3-yl]ethoxy]benzylidene]-2,4-thiazolidinedione (Compound 6M).

The NMR data for the Compounds 6A to 6M prepared in the Preparation Example 5 and this Preparation Example are shown in Table 2.

dihydro-2H-1,3-benzoxazin-3-yl)ethoxy]benzylidene]-2,4-thiazolidinedione (Compound 6A), the following compounds were used as the raw material compounds:
5-[4-[3-(4-oxo-3,4-dihydro-2H-1,3-benzoxazin-3-yl)propoxy]benzylidene]-2,4-thiazolidinedione (Compound 6B),
5-[4-[2-(2,2-dimethyl-4-oxo-3,4-dihydro-2H-1,3-benzoxazin-3-yl)ethoxy]benzylidene]-2,4-thiazolidinedione (Compound 6C),

TABLE 2

| Compound No. | (R¹)m | R² | R³ | R⁴ | R⁵ | X | n | ¹H-NMR(DMSO-d₆, δ) |
|---|---|---|---|---|---|---|---|---|
| 6A | — | H | H | H | H | O | 1 | 3.99(2H, t) 4.28(2H, t) 5.37(2H, s) 6.96–6.99(3H, m) 7.12(1H, ddd) 7.42–7.47(3H, m) 7.78(1H, s) 7.96(1H, dd) (CDCl₃) |
| 6B | — | H | H | H | H | O | 2 | 2.04(2H, t) 3.64(2H, t) 4.11(2H, t) 5.33(2H, s) 7.05(1H, m) 7.07(2H, d) 7.16(1H, t) 7.50(1H, m) 7.53(2H, d) 7.73(1H, s) 7.79(1H, dd) 12.40(1H, br) |
| 6C | — | Me | Me | H | H | O | 1 | 1.68(6H, s) 3.87(2H, t) 4.25(2H, t) 6.98(1H, d) 7.09–7.16(3H, m) 7.50–7.57(3H, m) 7.74(1H, s) 7.79(1H, ddd) 12.44(1H, brs) |
| 6D | — | Me | H | H | H | O | 1 | 1.55(3H, d) 3.67–3.72(1H, m) 3.99–4.05(1H, m) 4.25–4.28(2H, m) 5.77(1H, dd) 7.01(1H, d) 7.10–7.14(3H, m) 7.50–7.56(3H, m) 7.44(1H, s) 7.77(1H, dd) 12.4(1H, brs) |
| 6E | 7-Me | H | H | H | H | O | 1 | 2.33(3H, s) 3.86(2H, t) 4.22(2H, t) 5.37(2H, s) 6.87(1H, s) 6.96(1H, d) 7.08(2H, d) 7.50(2H, d) 7.56(1H, s) 7.68(1H, d) |
| 6F | 6-OMe | H | H | H | H | O | 1 | 3.76(3H, s) 3.88(2H, t) 4.25(2H, s) 5.35(2H, s) 7.10(1H, d) 7.09–7.14(3H, m) 7.27(1H, d) 7.54(2H, d) 7.73(1H, s) 12.45(1H, brs) |
| 6G | 8-OMe | H | H | H | H | O | 1 | NMR not measured. |
| 6H | 6-Cl | H | H | H | H | O | 1 | NMR not measured. |
| 6I | 7-OMe | H | H | H | H | O | 1 | NMR not measured. |
| 6J | 6-NO₂ | H | H | H | H | O | 1 | 3.92(2H, t) 4.28(2H, t) 5.59(2H, s) 7.12(2H, d) 7.32(1H, d) 7.54(2H, d) 7.71(1H, s) 8.36(1H, dd) 8.54(1H, d) 12.42(1H, brs) |
| 6K | — | H | H | H | H | 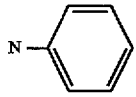 | 1 | 3.92(2H, t) 4.23(2H, t) 5.18(2H, s) 6.66–7.52(12H, m) 7.76(1H, s) 8.04(1H, dd) 8.93(1H, br) (CDCl₃) |
| 6L | — | H | H | H | H | N—Me | 1 | 2.86(3H, s) 3.26(1H, s) 3.84(2H, t) 4.26(2H, t) 4.60(2H, s) 6.80(1H, dd) 6.84(1H, ddd) 7.13(2H, d) 7.40(1H, ddd) 7.54(2H, d) 7.73(1H, s) 7.74(1H, dd) |
| 6M | — | H | H | H | H | 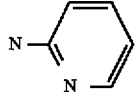 | 1 | 3.97(2H, t) 4.24(2H, t) 5.60(2H, s) 6.62–7.81(11H, m) 8.09(1H, dd) 8.36(1H, dd) 9.53(1H, br) (CDCl₃) |

Example 1

Preparation of 5-[4-[2-(4-oxo-3,4-dihydro-2H-1,3-benzoxazin-3-yl)benzyl]-2,4-thiazolidinedione (Invention Compound 1A)

0.99 g (2.5 mM) of 5-[4-[2-(4-oxo-3,4-dihydro-2H-1,3-benzoxazin-3-yl)ethoxy]benzylidene]-2,4-thiazolidinedione (Compound 6A) was suspended in 40 ml of 1,4-dioxane. 1.0 g of palladium-carbon (10%) was added to the suspension and the mixture was reacted for four hours in a hydrogen stream under 4 atmospheric pressures at 100° C. After the reaction, the palladium-carbon was removed by filtration while the reaction mixture was hot. This palladium-carbon was washed with hot ethyl acetate to collected the washing. The washing and the filtrate were combined and concentrated under reduced pressure. The residue was dissolved with hot ethyl acetate and gradually returned to room temperature. The resulting crystals were collected by filtration and washed with a small amount of ethyl acetate. The crystals were dried under reduced pressure at 60° C. to obtain 0.97 g (yield 96%) of the title compound as colorless crystals.

Example 2

Reactions were carried out in the same manner as the Example 1, except that instead of the 5-[4-[2-(4-oxo-3,4-

5-[4-[2-(2-methyl-4-oxo-3,4-dihydro-2H-1,3-benzoxazin-3-yl)ethoxy]benzylidene]-2,4-thiazolidinedione (Compound 6D),
5-[4-[2-(7-methyl-4-oxo-3,4-dihydro-2H-1,3-benzoxazin-3-yl)ethoxy]benzylidene]-2,4-thiazolidinedione (Compound 6E),
5-[4-[2-(6-methoxy-4-oxo-3,4-dihydro-2H-1,3-benzoxazin-3-yl)ethoxy]benzylidene]-2,4-thiazolidinedione (Compound 6F),
5-[4-[2-(8-methoxy-4-oxo-3,4-dihydro-2H-1,3-benzoxazin-3-yl)ethoxy]benzylidene]-2,4-thiazolidinedione (Compound 6G),
5-[4-[2-(6-chloro-4-oxo-3,4-dihydro-2H-1,3-benzoxazin-3-yl)ethoxy]benzylidene]-2,4-thiazolidinedione (Compound 6H),
5-[4-[2-(7-methoxy-4-oxo-3,4-dihydro-2H-1,3-benzoxazin-3-yl)ethoxy]benzylidene]-2,4-thiazolidinedione (Compound 6I),
5-[4-[2-(6-nitro-4-oxo-3,4-dihydro-2H-1,3-benzoxazin-3-yl)ethoxy]benzylidene]-2,4-thiazolidinedione (Compound 6J),
5-[4-[2-(4-oxo-1-phenyl-1,2,3,4-tetrahydroquinazolin-3-yl)ethoxy]benzylidene]-2,4-thiazolidinedione (Compound 6K),
5-[4-[2-(4-oxo-1-methyl-1,2,3,4-tetrahydroquinazolin-3-yl)ethoxy]benzylidene]-2,4-thiazolidinedione (Compound 6L), and 5-[4-[2-[4-oxo-1-(2-pyridyl)-1,2,3,4-tetrahydroquinazolin-3-yl]ethoxy]benzylidene]-2,4-thiazolidinedione (Compound 6M), to respectively produce the following compounds:

5-[4-[3-(4-oxo-3,4-dihydro-2H-1,3-benzoxazin-3-yl)propoxy]benzyl]-2,4-thiazolidinedione (Invention Compound, 1B), 5-[4-[2-(2,2-dimethyl-4-oxo-3,4-dihydro-2H-1,3-benzoxazin-3-yl)ethoxy]benzyl]-2,4-thiazolidinedione (Invention Compound 1C), 5-[4-[2-(2-methyl-4-oxo-3,4-dihydro-2H-1,3-benzoxazin-3-yl)ethoxy]benzyl]-2,4-thiazolidinedione (Invention Compound 1D), 5-[4-[2-(7-methyl-4-oxo-3,4-dihydro-2H-1,3-benzoxazin-3-yl)ethoxy]benzyl]-2,4-thiazolidinedione (Invention Compound 1E), 5-[4-[2-(6-methoxy-4-oxo-3,4-dihydro-2H-1,3-benzoxazin-3-yl)]ethoxy]benzyl]-2,4-thiazolidinedione (Invention Compound 1F), 5-[4-[2-(8-methoxy-4-oxo-3,4-dihydro-2H-1,3-benzoxazin-3-yl)ethoxy]benzyl]-2,4-thiazolidinedion (Invention Compound 1G), 5-[4-[2-(6-chloro-4-oxo-3,4-dihydro-2H-1,3-benzoxazin-3-yl)ethoxy]benzyl]-2,4-thiazolidinedione (Invention Compound 1H), 5-[4-[2-(7-methoxy-4-oxo-3,4-dihydro-2H-1,3-benzoxazin-3-yl)ethoxy]benzyl]-2,4-thiazolidinedione (Invention Compound 1I), 5-[4-[2-(6-amino-4-oxo-3,4-dihydro-2H-1,3-benzoxazin-3-yl)ethoxy]benzyl]-2,4-thiazolidinedione (Invention Compound 1J), 5-[4-[2-(4-oxo-1-phenyl-1,2,3,4-tetrahydroquinazolin-3-yl)ethoxy]benzyl]-2,4-thiazolidinedione (Invention Compound 1K), 5-[4-[2-(1-methyl-4-oxo-1,2,3,4-tetrahydroquinazolin-3-yl)ethoxy]benzyl]-2,4-thiazolidinedione (Invention Compound 1L), and 5-[4-[2-[4-oxo-1-(2-pyridyl)-1,2,3,4-tetrahydroquinazolin-3-yl]ethoxy]benzyl-2,4-thiazolidinedione (Invention Compound 1M).

The NMR data for the Invention Compound 1A to Invention Compound 1M prepared in Examples 1 and 2 are shown in Tables 3(1) and 3 (2).

TABLE 3(1)

| Compound No. | $(R^1)_m$ | $R^2$ | $R^3$ | $R^4$ | $R^5$ | X | n | m.p. °C. | $^1$H-NMR(CDCl$_3$, δ) |
|---|---|---|---|---|---|---|---|---|---|
| 1A | — | H | H | H | H | O | 1 | 136–137 | 3.04(1H, dd), 3.30(1H, dd), 3.85(2H, t), 4.13(2H, t), 4.83(1H, dd), 5.39(2H, s), 6.90(2H, d), 7.05(1H, d), 7.13–7.17(3H, m), 7.52(1H, ddd), 7.80(1H, dd) |
| 1B | — | H | H | H | H | O | 2 | Amorphous | 2.14(2H, q), 3.11(1H, dd), 3.44(1H, dd), 3.73(2H, t), 4.04(2H, t), 4.49(1H, dd), 5.20(2H, s), 6.83–6.87(1H, m), 6.85(2H, d), 6.96(1H, dd), 7.10–7.15(2H, m), 7.14(2H, d) |
| 1C | — | Me | Me | H | H | O | 1 | 150–151.5 | 1.74(6H, s), 3.09(1H, dd), 3.44(1H, dd), 3.91(2H, t), 4.20(2H, t), 4.48(1H, dd), 6.85–6.90(3H, m), 7.06(1H, m), 7.13(2H, d), 7.41–7.46(1H, m), 7.92(1H, dd), 8.68(1H, br s) |
| 1D | — | Me | H | H | H | O | 1 | 151–152 | 1.66(3H, d), 3.09(1H, dd), 3.43(1H, dd), 3.66–3.72(1H, m), 4.10–4.25(3H, m), 4.48(1H, dd), 5.64–5.69(1H, m), 6.84(2H, d), 6.93(1H, d), 7.13(2H, d), 7.06–7.10(1H, m), 7.41–7.45(1H, m), 7.93(1H, dd) |
| 1E | 7-Me | H | H | H | H | O | 1 | 150–151.5 | 2.36(3H, s), 3.09(1H, dd), 3.43(1H, dd), 3.93(2H, t), 4.17(2H, t), 4.47(1H, dd), 5.33(2H, s), 6.77(1H, s), 6.82(2H, d), 6.91(1H, d), 7.14(2H, d), 7.82(1H, d) |
| 1F | 6-OMe | H | H | H | H | O | 1 | 180–181.5 | 3.10(1H, dd), 3.43(1H, dd), 3.81(3H, s), 3.95(2H, t), 4.18(2H, t), 4.48(1H, dd), 5.32(2H, s), 6.83(2H, d), 6.90(1H, d), 7.02(1H, dd), 7.14(2H, d), 7.41(1H, d) |

TABLE 3(2)

| Compound No. | $(R^1)_m$ | $R^2$ | $R^3$ | $R^4$ | $R^5$ | X | n | m.p. °C. | $^1$H-NMR(CDCl$_3$, δ) |
|---|---|---|---|---|---|---|---|---|---|
| 1G | 8-OMe | H | H | H | H | O | 1 | 95.5–96.0 | 3.10(1H, dd) 3.43(1H, dd) 3.90(3H, s) 3.94–3.97(2H, m) 4.11–4.19(2H, m) 4.48(1H, dd) 5.41(2H, s) 6.82(2H, d) 7.02–7.08(2H, m) 7.13(2H, d) 7.55(1H, dd) |
| 1H | 6-Cl | H | H | H | H | O | 1 | 125–126 | 3.11(1H, dd) 3.42(1H, dd) 3.95(2H, t) 4.17(2H, t) 4.49(1H, dd) 5.36(2H, s) 6.82(2H, d) 6.93(1H, d) 7.14(2H, 2H, d) 7.38(1H, dd) 7.91(1H, d) |
| 1I | 7-OMe | H | H | H | H | O | 1 | 141–142.5 | 3.10(1H, dd) 3.43(1H, dd) 3.83(3H, s) 3.93(2H, t) 4.16(2H, t) 4.48(1H, dd) 5.34(2H, s) 6.44(1H, d) 6.65(1H, dd) 6.83(2H, d) 7.14(2H, d) 7.86(1H, d) |
| 1J | 6-NH$_2$ | H | H | H | H | O | 1 | 205–206 | 3.04(1H, dd) 3.30(1H, dd) 3.80(2H, t) 4.16(2H, t) 4.83(1H, dd) 5.23(2H, s) 6.73–6.74(2H, m) 6.89(2H, d) 7.00–7.01(1H, m) 7.15(2H, d) (DMSO-d$_6$) |
| 1K | — | H | H | H | H | 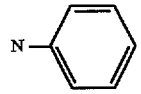 | 1 | Amorphous | 3.07(1H, dd) 3.42(1H, dd) 3.90(2H, t) 4.14(2H, t) 4.46(1H, dd) 5.17(2H, s) 6.64(2H, d) 6.90(1H, dd) 7.00(1H, ddd) 7.07(2H, d) 7.13–7.18(3H, m) 7.29(1H, ddd) 7.34–7.38(2H, m) 8.03(1H, dd) 8.70(1H, br) |
| 1L | — | H | H | H | H | N—Me | 1 | Amorphous | 2.90(3H, s) 3.09(1H, dd) 3.42(1H, dd) 3.92(2H, t) 4.20(2H, t) 4.47(1H, dd) 4.62(2H, s) 6.69(1H, d) 6.84(2H, d) 6.89(1H, ddd) 7.13(2H, d) 7.39(1H, ddd) 7.95(1H, dd) |

TABLE 3(2)-continued

| Compound No. | (R¹)m | R² | R³ | R⁴ | R⁵ | X | n | m.p. °C. | ¹H-NMR(CDCl₃, δ) |
|---|---|---|---|---|---|---|---|---|---|
| 1M | — | H | H | H | H | 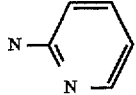 | 1 | Amorphous | 3.07(1H, dd) 3.40(1H, dd) 3.92(2H, t) 4.14(2H, t) 4.45(1H, dd) 5.57(2H, s) 6.67(2H, d) 6.89(1H, ddd) 7.05–7.07(3H, m) 7.19(1H, ddd) 7.33(1H, d) 7.44(1H, ddd) 7.51(1H, ddd) 8.08(1H, dd) 8.35(1H, dd) 8.92(1H, br) |

Preparation Example 7

Preparation of 2,2-dimethyl-4-oxo-3,4-dihydro-2H-1,3-benzoxazine (Compound 12)

6.86 g (50 mmol) of salicylamide was suspended in 100 ml of acetone dimethylacetal. After the addition of 2.85 g (15 mmol) of p-toluenesulfonic acid, the mixture was heated to reflux for two hours. The resulting reaction mixture was evaporated under reduced pressure. After the addition of ethyl acetate, the solvent was washed twice with a saturated aqueous solution of sodium hydrogen carbonate and once with brine. The ethyl acetate layer was dried over anhydrous sodium sulfate and the solvent was removed by evaporation under reduced pressure, to obtain 8.94 g (quantitative) of the title compound as light yellow needle-like crystals.

¹H-NMR (CDCl₃)δ: 1.66(6H, s), 6.86–7.12(2H, m), 7.39 (1H, m), 7.86–7.95(2H, m)

Preparation Example 8

Preparation of 4-[2-(2,2-dimethyl-4-oxo-3,4-dihydro-2H-1,3-benzoxazin-3-yl)ethoxy]benzaldehyde (Compound 4C)

100 ml of dimethylformamide was added to 1.77 g of 2,2-dimethyl-4-oxo-3,4-dihydro-2H-1,3-benzoxazine, 2.56 g of 2-(4-formylphenoxy) ethyl methanesulfonate, and 2.07 g of potassium carbonate. The mixture was stirred at 80° C. over an oil bath for six hours. The reaction mixture was poured into water, extracted with ethyl acetate, and washed with brine. The ethyl acetate layer was dried over anhydrous sodium sulfate, the solvent was removed by evaporation under reduced pressure, and the residue was purified by a silica gel column, thereby obtaining 0.68 g (yield 20.9%) of the title compound as colorless crystals.

Preparation Example 9

Compound 4D was prepared in the same manner as in the Preparation Examples 7 and 8, except that acetone dimethylacetal was replaced by acetaldehyde dimethylacetal. The NMR data for the Compound 4C prepared in the Preparation Example 8 and the compound 4D prepared in this Preparation Example 9 were the same as those shown in the Table for the Preparation Example 4.

Example 3

The following compounds will be prepared by the methods described in the above Examples and Preparation Examples.

5-[4-[2-(5-Methyl-4-oxo-3,4-dihydro-2H-1,3-benzoxazin-3-yl)ethoxy]benzyl]-2,4-thiazolidinedione
5-[4-[2- (6-Ethyl-4-oxo-3,4-dihydro-2H-1,3-benzoxazin-3-yl)ethoxy]benzyl]-2,4-thiazolidinedione
5-[4-[2-(7-Propyl-4-oxo-3,4-dihydro-2H-1,3-benzoxazin-3-yl)ethoxy]benzyl]-2,4-thiazolidinedione
5-[4-[2-(7-Isopropyl-4-oxo-3,4-dihydro-2H-1,3-benzoxazin-3-yl)ethoxy]benzyl]-2,4-thiazolidinedione
5-[4-[2-(8-Butyl-4-oxo-3,4-dihydro-2H-1,3-benzoxazin-3-yl)ethoxy]benzyl]-2,4-thiazolidinedione
5-[4-[2-(5-Methoxy-4-oxo-3,4-dihydro-2H-1,3-benzoxazin-3-yl)ethoxy]benzyl]-2,4-thiazolidinedione
5-[4-[2-(6-Ethoxy-4-oxo-3,4-dihydro-2H-1,3-benzoxazin-3-yl)ethoxy]benzyl]-2,4-thiazolidinedione
5-[4-[2-(7-Propoxy-4-oxo-3,4-dihydro-2H-1,3-benzoxazin-3-yl)ethoxy]benzyl]-2,4-thiazolidinedione
5-[4-[2-(8-Butoxy-4-oxo-3,4-dihydro-2H-1,3-benboxazin-3-yl)ethoxy]benzyl]-2,4-thiazolidinedione
5-[4-[2-(6,7-Dimethyl-4-oxo-3,4-dihydro-2H-1,3-benzoxazin-3-yl)ethoxy]benzyl]-2,4-thiazolidinedione
5-[4-[2- (6,7-Dimethoxy-4-oxo-3,4-dihydro-2H-1,3-benzoxazin-3-yl)ethoxy]benzyl]-2,4-thiazolidinedione
5-[4-[2-(6,7,8-Trimethyl-4-oxo-3,4-dihydro-2H-1,3-benzoxazin-3-yl)ethoxy]benzyl]-2,4-thiazolidinedione
5-[4-[2-(5-Bromo-4-oxo-3,4-dihydro-2H-1,3-benzoxazin-3-yl)ethoxy]benzyl]-2,4-thiazolidinedione
5-[4-[2-(6-Fluoro-4-oxo-3,4-dihydro-2H-1,3-benzoxazin-3-yl)ethoxy]benzyl]-2,4-thiazolidinedione
5-[4-[2-(6-Iodo-4-oxo-3,4-dihydro-2H-1,3-benzoxazin-3-yl)ethoxy]benzyl]-2,4-thiazolidinedione
5-[4-[2-(6,7-Dichloro-4-oxo-3,4-dihydro-2H-1,3-benzoxazin-3-yl)ethoxy]benzyl]-2,4-thiazolidinedione
5-[4-[2- (6-Trifluoromethyl-4-oxo-3,4-dihydro-2H-1,3-benzoxazin-3-yl)ethoxy]benzyl]-2,4-thiazolidinedione
5-[4-[2-(7-Hydroxy-4-oxo-3,4-dihydro-2H-1,3-benzoxazin-3-yl)ethoxy]benzyl]-2,4-thiazolidinedione
5-[4-[2-(6,7-Dihydroxy-4-oxo-3,4-dihydro-2H-1,3-benzoxazin-3-yl)ethoxy]benzyl]-2,4-thiazolidinedione
5-[4-[2-(6-Benzyloxy-4-oxo-3,4-dihydro-2H-1,3-benzoxazin- 3-yl)ethoxy]benzyl]-2,4-thiazolidinedione
5-[4-[2-(6-Cyano-4-oxo-3,4-dihydro-2H-1,3-benzoxazin-3-yl)ethoxy]benzyl]-2,4-thiazolidinedione
5-[4-[2- (6-Carbamoyl-4-oxo-3,4-dihydro-2H-1,3-benzoxazin-3-yl)ethoxy]benzyl]-2,4-thiazolidinedione
5-[4-[2-(6-Acetyl-4-oxo-3,4-dihydro-2H-1,3-benzoxazin-3-yl)ethoxy]benzyl]-2,4-thiazolidinedione
5-[4-[2-(Butyryl-4-oxo-3,4-dihydro-2H-1,3-benzoxazin-3-yl)ethoxy]benzyl]-2,4-thiazolidinedione
5-[4-[2- (6-Nitro-4-oxo-3,4-dihydro-2H-1,3-benzoxazin-3-yl)ethoxy]benzyl]-2,4-thiazolidinedione
5-[4-[2-(8-Nitro-4-oxo-3,4-dihydro-2H-1,3-benzoxazin-3-yl)ethoxy]benzyl]-2,4- thiazolidinedione
3-[2-[4- (2,4-Dioxo-thiazolidine-5-ylmetyl)phenoxy]ethyl]-4-oxo-3,4 -dihydro-2H-1,3-benzoxazine-6-carboxylic acid
5-[4-[2-(6-Sulphamido-4-oxo-3,4-dihydro-2H-1,3-benzoxazin-3-yl)ethoxy]benzyl]-2,4-thiazolidinedione
5-[4-[3- (7-Methyl-4-oxo-3,4-dihydro-2H-1,3-benzoxazin-3-yl)propoxy]benzyl]-2,4-thiazolidinedione
5-[4 -[3-(8-Methoxy-4-oxo-3,4-dihydro-2H-1,3-benzoxazin-3-yl)propoxy]benzyl]-2,4-thiazolidinedione
5-[4-[3-(6-Chloro-4-oxo-3,4-dihydro-2H-1,3-benzoxazin-3-yl)propoxy]benzyl]-2,4-thiazolidinedione
5-[4-[3-(6-Amino-4-oxo-3 4-dihydro-2H-1,3-benzoxazin-3-yl)propoxy]benzyl]-2,4-thiazolidinedione
5-[4-[3-(6-Cyano-4-oxo-3,4-dihydro-2H-1,3-benzoxazin-3-yl)propoxy]benzyl]-2,4-thiazolidinedione 5-[4-[3-(6-Acetyl-4-oxo-3,4-dihydro-2H-1,3-benzoxazin-3-yl)propoxy]benzyl]-2,4-thiazolidinedione
5-[4-[3- (6-Nitro-4-oxo-3,4-dihydro-2H-1,3-benzoxazin-3-yl)propoxy]benzyl]-2,4-thiazolidinedione.
5-[4-[3- (6-Sulphamido-4-oxo-3,4-dihydro-2H-1,3-benzoxazin-3-yl)propoxy]benzyl]-2,4-thiazolidinedione
5-[4-[3-(8-Benzyloxy-4-oxo-3,4-dihydro-2H-1,3-benzoxazin-3-yl)propoxy]benzyl]-2,4-thiazolidinodione
3-[3-[4-(2,4-Dioxo-thiazolidine-5-ylmetyl)phenoxy]propyl]-4-oxo-3,4-dihydro-2H-1,3-benzoxazine-6- carboxylic acid
5-[4-[2-(6-Methyl-4-oxo-3,4-dihydro-2H-1,3-benzoxazin-3-yl)propoxy]benzyl]-2,4-thiazolidinedione
5-[4-[2-(6-Chloro-4-oxo-3,4-dihydro-2H-1,3-benzoxazin-3-yl)propoxy]benzyl]-2,4-thiazolidinedione
5-[4-[2-(6-Cyano-4-oxo-3,4-dihydro-2H-1,3-benzoxazin-3-yl)propoxy]benzyl]-2,4-thiazolidinedione
5-[4-[4-(6-Nitro-4-oxo-3,4-dihydro-2H-1,3-benzoxazin-3-yl)butoxy]benzyl]-2,4-thiazolidinedione
5-[4-[4-(6-Amino-4-oxo-3,4-dihydro-2H-1,3-benzoxazin-3-yl)butoxy]benzyl]-2,4- thiazolidinedione
5-[4-[2-(6-Methyl-4-oxo-3,4-dihydro-2H-1,3-benzoxazin-3-yl)-2-methylpropoxy]benzyl]-2,4-thiazolidinedione
5-[4-[2-(2,6-Dimethyl-4-oxo-3,4-dihydro-2H-1,3-benzoxazin-3-yl)-2-methylpropoxy]benzyl]-2,4-thiazolidinedione
5-[4-[2-[4-Oxospiro(3,4-dihydro-2H-1,3-benzoxazin-2,1'-cyclopentane)-3-yl]-2-methylpropoxy]benzyl]-2,4-thiazolidinedione
5-[4-[2-(6-Methyl-4-oxo-1-phenyl-1,2,3,4-tetrahydroquinazolin-3-yl)ethoxy]benzyl]-2,4-thiazolidinedione
5-[4-[2-(8-Methoxy-4-oxo-1-phenyl-1,2,3,4-tetrahydroquinazolin-3-yl) ethoxy]benzyl]-2,4-thiazolidinedione
5-[4-[2-(6-Amino-4-oxo-1-phenyl-1,2,3,4-tetrahydroquinazolin-3-yl)ethoxy]benzyl]-2,4-thiazolidinedione
5-[4-[2-(6-Chloro-4-oxo-1-phenyl-1,2,3,4-tetrahydroquinazolin-3-yl)ethoxy]benzyl]-2,4-thiazolidinedione
5-[4-[2-(6-Cyano-4-oxo-1-phenyl-1,2,3,4-tetrahydroquinazolin-3-yl)ethoxy]benzyl]-2,4-thiazolidinedione
5-[4-[2-(6,7-Dimethyl-4-oxo-1-phenyl-1,2,3,4-tetrahydroquinazolin-3-yl)ethoxy]benzyl]-2,4-thiazolidinedione
5-[4-[2-(6,7-Dimethoxy-4-oxo-1-phenyl-1,2,3,4-tetrahydroquinazolin-3-yl)ethoxy]benzyl]-2,4-thiazolidinedione
5-[4-[2-(6-Nitro-4-oxo-1-phenyl-1,2,3,4-tetrahydroquinazolin-3-yl)ethoxy]benzyl]-2,4-thiazolidinedione
5-[4-[3-(6-Methyl-4-oxo-1-phenyl-1,2,3,4-tetrahydroquinazolin-3-yl)propoxy]benzyl]-2,4-thiazolidinedione
5-[4-[3-(8-Methoxy-4-oxo-1-phenyl -1,2,3,4-tetrahydroquinazolin-3 -yl) propoxy]benzyl]-2,4-thiazolidinedione
5-[4-[3-(6-Nitro-4-oxo-1-phenyl-1,2,3,4-tetrahydroquinazolin-3-yl)propoxy]benzyl]-2,4-thiazolidinedione
5-[4-[3-(6-Chloro-4-oxo-1-phenyl-1,2,3,4-tetrahydroquinazolin-3-yl)propoxy]benzyl]-2,4-thiazolidinedione
5-[4-[3-(7-Benzyloxy-4-oxo-1-phenyl-1,2,3,4-tetrahydroquinazolin-3-yl)propoxy]benzyl]-2,4-thiazolidinedione
5-[4-[3-(6-Cyano-4-oxo-1-phenyl-1,2,3,4-tetrahydroquinazolin-3-yl) propoxy]benzyl]-2,4-thiazolidinedione
5-[4-[3-(6-Carbamoyl-4-oxo-1-phenyl-1,2,3,4-tetrahydroquinazolin-3-yl)propoxy]benzyl]-2,4-thiazolidinedione
5-[4-[2-(7-Methyl-4-oxo-1-phenyl-1,2,3,4-tetrahydroquinazolin-3-yl)propoxy]benzyl]-2,4-thiazolidinedione
5-[4-[2-(7-Methoxy-4-oxo-1-phenyl-1,2,3,4-tetrahydroquinazolin-3-yl)propoxy]benzyl]-2,4-thiazolidinedione
5-[4-[2-(6-Chloro-4-oxo-1-phenyl-1,2,3,4-tetrahydroquinazolin-3-yl)propoxy]benzyl]-2,4-thiazolidinedione
5-[4-[2- (4-Oxo-1-phenyl-1,2,3,4-tetrahydroquinazolin-3-yl)-2-methylpropoxy]benzyl]-2,4-thiazolidinedione
5-[4-[2-(6-Methyl-4-oxo-1-phenyl-1,2,3,4-tetrahydroquinazolin-3-yl)-2-methylpropoxy]benzyl]-2,4-thiazolidinedione
5-[4-[2-2-Methyl-1-(4-methylphenyl)-4-oxo-1-phenyl-1,2,3,4-tetrahydroquinazolin-3-yl]propoxy]benzyl]-2,4-thiazolidinedione
5-[4-[2-[2-Methyl-1-(4-methylphenyl) -4-oxo-1-phenyl-1,2,3,4-tetrahydroquinazolin-3-yl]-2-methylpropoxy]benzyl]-2,4- thiazolidinedione
5-[4-[2-[1-(4-Methylphenyl) -4-oxospiro(1,2,3,4-tetrahydroquinazolin-2,1'-cyclopentane)-3-yl]-2-methylpropoxy]benzyl]- 2,4-thiazolidinedione
5-[4-[2-[1-(4-Hydroxyphenyl)-4-oxospiro(1,2,3,4-tetrahydroquinazolin-2,1'-cyclopentane)-3-yl]-2-methylpropoxy]benzyl]-2,4-thiazolidinedione
5-[4-[2- (4-Oxo-3,4-dihydro-2H-1,3-benzthiazin-3-yl) ethoxy]benzyl]-2,4-thiazolidinedione
5-[4-[2-(5-Methyl-4-oxo-3,4-dihydro-2H-1,3-benzthiazin-3-yl)ethoxy]benzyl]-2,4-thiazolidinedione
5-[4-[2-(6-Methoxy-4-oxo-3,4-dihydro-2H-1,3-benzthiazin-3-yl)ethoxy]benzyl]-2,4-thiazolidinedione
5-[4-[2-(6-Nitro-4-oxo-3,4-dihydro-2H-1,3-benzthiazin-3-yl)ethoxy]benzyl]-2,4-thiazolidinedione
5-[4-[2-(6-Chloro-4-oxo-3,4-dihydro-2H-1,3-benzthiazin-3-yl)ethoxy]benzyl]-2,4-thiazolidinedione
5-[4-[2-(6-Cyano-4-oxo-3,4-dihydro-2H-1,3-benzthiazin-3-yl)ethoxy]benzyl]-2,4-thiazolidinedione
3-[3-[4-(2,4-Dioxo-thiazolidine-5-ylmetyl) phenoxy]propyl]-4-oxo-3,4-dihydro-2H-1,3-benzthiazine-6-carboxylic acid
5-[4-[3-(4-Oxo-3,4-dihydro-2H-1,3-benzthiazin-3-yl)propoxy]benzyl]-2,4-thiazolidinedione
5-[4-[2-(4-Oxo-3,4-dihydro-2H-1,3-benzthiazin-3-yl)propoxy]benzyl]-2,4-thiazolidinedione
5-[4-[2-(2-Methyl-4-oxo-3,4-dihydro-2H-1,3-benzthiazin-3-yl)ethoxy]benzyl]-2,4-thiazolidinedione
5-[4-[2-(2,6-Dimethyl-4-oxo-3,4-dihydro-2H-1,3-benzthiazin-3-yl)ethoxy]benzyl]-2,4-thiazolidinedione
5-[4-[2-(2-Methyl-6-methoxy-4-oxo-3,4-dihydro-2H-1,3-benzthiazin-3-yl)ethoxy]benzyl]-2,4-thiazolidinedione
5-[4-[2-(2,2-Dimethyl-4-oxo-3,4-dihydro-2H-1,3-benzthiazin-3-yl)ethoxy]benzyl]-2,4-thiazolidinedione
5-[4-[2-(2,2,6-Trimethyl-4-oxo-3,4-dihydro-2H-1,3-benzthiazin-3-yl)ethoxy]benzyl]-2,4-thiazolidinedione Test Example A test for the evaluation of non-insulin-dependent diabetes mellitus (NIDDM) by model animal was carried out using several benzoazine derivatives of the present invention. Troglitazone (Tr) was used as a comparative compound.

<Experimental method>

Groups of male mice (KK-AY/TaJcl mice, supplied by Crea Company), aged 7 or 8 weeks, each group consisting of five, were used for the test. The mice were separately bred for two weeks and those with a blood glucose value of over 300 mg/dl were used. The mice were fed with a feed containing a prescribed amount of the compounds of the present invention or the comparative compound for four days. After four days, blood was collected from each animal to measure the blood glucose value, plasma triglyceride, and plasma insulin value (Measured Value). The blood glucose value, plasma triglyceride, and plasma insulin value (Control Values) were also measured on blood samples Collected from mice of the control group, to which no compounds of the present invention or the contrastive compound were administered.

The blood glucose value was measured using a blood glucose measurement unit Mediace Blood Glucose Measurement Reader GR-100™ (manufactured by Terumo Corp.) or Glucose B Test Wako™ (manufactured by Wako Pure Chemical Industries Ltd.), the plasma triglyceride was measured using Triglyceride E Test Wako™ (manufactured by Wako Pure Chemical Industries Ltd.), and the plasma insulin was measured using Glazyme Insulin-EIA™ (manufactured by Wako Pure Chemical Industries Ltd.).

The reduction rate for each measurement when the compound of the present invention or the contrastire compound was used as compared with the measured value for the control group was calculated according to the following formula.

$$\text{Reduction Rate (\%)} = \frac{\text{Control Value} - \text{Measure Value}}{\text{Control Value}} \times 100$$

The results are shown in Table 4.

TABLE 4

| Compound | Dose (mg/kg/day) | Blood glucose reduction (%) | Plasma insulin reduction (%) | Plasma triglyceride reduction (%) |
|---|---|---|---|---|
| 1A | 9.8 | 65.8 | 67.4 | 75.0 |
| 1D | 30.0 | 59.6 | 72.3 | 78.2 |
| 1E | 26.3 | 60.0 | 58.8 | 76.4 |
| 1F | 9.6 | 57.5 | 50.4 | 84.2 |
| 1G | 9.7 | 45.9 | 59.2 | 56.4 |
| 1H | 9.9 | 54.1 | 69.0 | 78.4 |
| 1I | 9.8 | 57.1 | 67.5 | 71.5 |
| 1L | 10.6 | 43.3 | 47.3 | 51.7 |
| Tr | 183.5 | 50.8 | 69.2 | 44.0 |

It can be seen from the results of Table 4 that the composition of the present invention exhibits superior effects for reducing blood glucose value, plasma insulin value, and plasma triglyceride value at a smaller dose as compared with the comparative compound.

Obviously, numerous modifications and variations of the present invention are possible in light of the above teachings. It is therefore to be understood that, within the scope of the appended claims, the invention may be practiced otherwise than as specifically described herein.

What is claimed is:

1. A benzoazine derivative represented by the following formula (1),

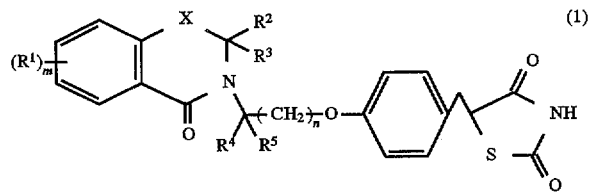

wherein $R^1$ represents an alkyl group, alkoxy group, halogen atom, halogenoalkyl group, amino group, hydroxy group, benzyloxy group which may have a substituent, cyano group, carbamoyl group, acyl group, nitro group, carboxy group, or sulfonamide group; $R^2$ and $R^3$ may be the same or different and each individually represents a hydrogen atom or an alkyl group, or $R^2$ and $R^3$ indicate in combination an alkylene group having 2–7 carbon atoms; $R^4$ and $R^5$ may be the same or different and each individually represents a hydrogen atom or an alkyl group; X denotes O, S, or N—$R^6$ (wherein $R^6$ represents a hydrogen atom, an alkyl group, or an aryl group or pyridyl group which may have a substituent); m is an integer from 0 to 4; and n is an integer from 1 to 3, or a salt of the benzoazine derivative.

2. A pharmaceutical composition comprising an effective amount of the benzoazine derivative or the salt thereof defined in claim 1 and pharmaceutically acceptable carriers.

3. The pharmaceutical composition according to claim 2, wherein the composition is used for preventing or treating diabetes, hyperlipidemia, and obesity.

4. A method for reducing a blood glucose value in a subject which comprises administering an effective amount of the benzoazine derivative or the salt thereof defined claim 1 to the subject.

* * * * *